US010987264B2

(12) United States Patent
Jiang et al.

(10) Patent No.: US 10,987,264 B2
(45) Date of Patent: Apr. 27, 2021

(54) COMBINATION RESPIRATORY THERAPY AND MATTRESS FUNCTIONALITY SYSTEM INTEGRATED INTO A PATIENT BED

(71) Applicant: HILL-ROM SERVICES PTE. LTD, Singapore (SG)

(72) Inventors: Cong Jiang, Singapore (SG); Wei T. Tan, Singapore (SG); Siew Ying Koh, Singapore (SG); Eugene Hong Kheng Kung, Singapore (SG); Nookarajesh Varma Sangadi, Singapore (SG); Yue Yun Wang, Columbus, IN (US); Aye Aung, Singapore (SG); Tak Wei David Teo, Singapore (SG); Chau Chong Ye, Singapore (SG); Amodh Gundlur Ramesh, Bangalore (IN); David J. Brzenchek, Harrison, OH (US); Jack Barney Sing, Batesville, IN (US); Steven V. McCaig, Greensburg, IN (US); Chee Keong Ng, Singapore (SG)

(73) Assignee: HILL-ROM SERVICES PTE. LTD., Singapore (SG)

( * ) Notice: Subject to any disclaimer, the term of this patent is extended or adjusted under 35 U.S.C. 154(b) by 344 days.

(21) Appl. No.: 16/032,427

(22) Filed: Jul. 11, 2018

(65) Prior Publication Data

US 2019/0021925 A1    Jan. 24, 2019

Related U.S. Application Data

(60) Provisional application No. 62/533,841, filed on Jul. 18, 2017.

(51) Int. Cl.
*A61G 7/00* (2006.01)
*A61G 7/05* (2006.01)
(Continued)

(52) U.S. Cl.
CPC ............ *A61G 7/0524* (2016.11); *A61G 7/012* (2013.01); *A61G 7/0514* (2016.11);
(Continued)

(58) Field of Classification Search
CPC .................................. A61G 7/00; A61G 7/05
(Continued)

(56) References Cited

U.S. PATENT DOCUMENTS

| 3,148,391 A | 9/1964 | Whitney |
| 3,653,083 A | 4/1972 | Lapidus |

(Continued)

FOREIGN PATENT DOCUMENTS

| GB | 1416697 | 12/1975 |
| WO | 2016/159889 A1 | 10/2016 |

OTHER PUBLICATIONS

Extended European Search Report for European Patent Application No. 18183802.0 dated Nov. 19, 2018; 8 pages.
(Continued)

*Primary Examiner* — Fredrick C Conley
(74) *Attorney, Agent, or Firm* — Barnes & Thornburg LLP

(57) ABSTRACT

A patient support apparatus includes a frame and a mattress positioned on the frame. A respiratory therapy device is coupled to the frame. The respiratory therapy device includes a blower having an inlet and an outlet, a patient interface, and a valve including a valve member that is rotatable through a first angular displacement in a first direction from a first position to a second position. The outlet of the blower is coupled to the patient interface so that positive pressure is provided to a patient's airway via the patient interface when the valve member is in the first position. The inlet of the blower is coupled to the patient interface so that negative pressure is provided to the
(Continued)

patient's airway via the patient interface when the valve member is in the second position.

26 Claims, 11 Drawing Sheets

(51) Int. Cl.
| | |
|---|---|
| *A61G 7/057* | (2006.01) |
| *A61M 16/20* | (2006.01) |
| *A61M 16/08* | (2006.01) |
| *A61M 11/06* | (2006.01) |
| *A61M 16/00* | (2006.01) |
| *A61G 7/012* | (2006.01) |
| *A61M 16/10* | (2006.01) |
| *A61M 16/06* | (2006.01) |

(52) U.S. Cl.
CPC ......... *A61G 7/05769* (2013.01); *A61M 11/06* (2013.01); *A61M 16/0009* (2014.02); *A61M 16/0066* (2013.01); *A61M 16/0833* (2014.02); *A61M 16/202* (2014.02); *A61G 7/05* (2013.01); *A61G 7/0506* (2013.01); *A61M 16/0006* (2014.02); *A61M 16/06* (2013.01); *A61M 16/107* (2014.02); *A61M 2016/0039* (2013.01); *A61M 2205/8206* (2013.01); *A61M 2209/082* (2013.01)

(58) Field of Classification Search
USPC .......................................................... 5/600
See application file for complete search history.

(56) References Cited

U.S. PATENT DOCUMENTS

| | | | |
|---|---|---|---|
| 3,757,366 A | 9/1973 | Sacher | |
| 4,225,989 A | 10/1980 | Corbett et al. | |
| 4,333,453 A * | 6/1982 | Rodder | A61M 16/20 128/205.24 |
| 4,391,009 A | 7/1983 | Schild et al. | |
| 5,189,742 A | 3/1993 | Schild | |
| 5,335,651 A | 8/1994 | Foster et al. | |
| 5,337,845 A | 8/1994 | Foster et al. | |
| 5,457,831 A | 10/1995 | Foster et al. | |
| 5,497,766 A | 3/1996 | Foster et al. | |
| 5,562,091 A | 10/1996 | Foster et al. | |
| 6,859,967 B2 | 3/2005 | Harrison et al. | |
| 7,469,432 B2 | 12/2008 | Chambers | |
| 7,909,033 B2 | 3/2011 | Faram | |
| 7,931,607 B2 | 4/2011 | Biondo et al. | |
| 8,108,957 B2 | 2/2012 | Richards et al. | |
| 8,539,952 B2 | 9/2013 | Carbone et al. | |
| 8,584,279 B2 | 11/2013 | Richards et al. | |
| 8,844,530 B2 | 9/2014 | Birnkrant | |
| 8,985,112 B2 | 3/2015 | Ikei et al. | |
| 9,272,115 B2 | 3/2016 | Bobey et al. | |
| 2008/0263776 A1 | 10/2008 | O'Reagan et al. | |
| 2010/0043143 A1 | 2/2010 | O'Reagan et al. | |
| 2011/0100360 A1 | 5/2011 | Faram | |
| 2015/0135436 A1* | 5/2015 | Stryker | A61G 7/1019 5/600 |
| 2016/0157631 A1 | 6/2016 | Milnes et al. | |
| 2017/0046620 A1 | 2/2017 | Morrison | |
| 2018/0085541 A1 | 3/2018 | Ye et al. | |

OTHER PUBLICATIONS

Notification of Reasons for Rejection for Japanese Patent Application No. 2018-133446 dated Oct. 2, 2019 and its English translation (9 pages).

* cited by examiner

COMBINATION RESPIRATORY THERAPY AND MATTRESS FUNCTIONALITY SYSTEM INTEGRATED INTO A PATIENT BED

CROSS-REFERENCE TO RELATED APPLICATIONS

This application claims priority to U.S. Provisional Patent Application Ser. No. 62/533,841, filed Jul. 18, 2017 and titled "COMBINATION RESPIRATORY THERAPY AND MATTRESS FUNCTIONALITY SYSTEM INTEGRATED INTO A PATIENT BED," which is herein incorporated by reference in its entirety.

TECHNICAL FIELD

The present disclosure relates to beds and respiratory therapy apparatuses having air flow valves and particularly, to air flow valves that are operable to apply varying levels of oscillating pressure to an airway of a patient or to apply pressure to a bladder of a patient support apparatus.

BACKGROUND

Respiratory therapy devices that provide positive pressure to a person's airway are known. For example, there are Continuous Positive Airway Pressure (CPAP) devices that apply positive pressure to a person's airway at a substantially constant level during the person's inhalation and exhalation. There are also Bi-Level CPAP devices that apply varying levels of positive pressure to a person, such as applying a first amount of positive pressure during inhalation and a second amount of positive pressure during exhalation.

Respiratory therapy devices that provide negative pressure or suction to a person's airway are also known. One category of such devices is mechanical insufflation/exsufflation (MIE) devices. These devices are sometimes referred to as cough assist devices. This is because application of positive pressure followed by application of negative pressure to a person's airway simulates a cough and assists the person in expelling mucus from their airway.

Respiratory therapy devices that are capable of applying both positive and negative pressure to a person's airway sometimes have a pressure source, such as a blower, and at least one valve that changes position to selectively connect either the outlet of the blower or the inlet of the blower to a patient interface, such as a mask or mouthpiece and related tubing, to apply the positive pressure or the negative pressure, respectively to the person's airway. Other respiratory therapy devices have separate positive pressure and negative pressure sources.

Additionally, bladders within a patient support apparatus are also known. Such bladders receive airflow from a blower to assist in patient movement or comfort. Generally, such bladders are filled with a blower that is separate from the blower utilized to operate the respiratory therapy device. Accordingly, the patient support apparatus may have multiple blowers attached thereto.

SUMMARY

The present disclosure includes one or more of the features recited in the appended claims and/or the following features which, alone or in any combination, may comprise patentable subject matter.

In one aspect of the disclosed embodiments, a patient support apparatus includes a frame having a head section, a seat section, and a foot section. A mattress is positioned on the frame and extends across the head section, seat section, and foot section. A respiratory therapy device is coupled to the frame. The respiratory therapy device includes a blower having an inlet and an outlet, a patient interface, and a valve including a valve member that is rotatable through a first angular displacement in a first direction from a first position to a second position. The outlet of the blower is coupled to the patient interface so that positive pressure is provided to a patient's airway via the patient interface when the valve member is in the first position. The inlet of the blower is coupled to the patient interface so that negative pressure is provided to the patient's airway via the patient interface when the valve member is in the second position.

In some embodiments, a housing may be coupled to the frame. The respiratory therapy device may be positioned within the housing. In some embodiments, a drawer that slides in and out of the housing may be provided. The respiratory therapy device may be positioned within the drawer. In some embodiments, the housing may have a wall having a port extending therethrough. The drawer may have a wall having a port coupled to a port of the respiratory therapy device. The port formed in the drawer may engage the port formed in the housing when the drawer is slide into the housing in a closed position. In some embodiments, a hose may couple the patient interface to the port formed in the housing. In some embodiments, a port may be formed in the frame. A port of the respiratory therapy device may be coupled to the port formed in the frame. In some embodiments, a hose may couple the port formed in the frame to the patient interface.

In some embodiments, a rotary valve may be coupled between a port of the respiratory therapy device and the patient interface. The rotary valve may be coupled to the patient interface, a left turn bladder of the mattress, a right turn bladder of the mattress, and at least one percussion and vibration bladder of the mattress. In some embodiments, the rotary valve may have a first rotary plate and a second rotary plate. When the second rotary plate is in a first position and the first rotary plate is in a first position, the blower may be operable to inflate the at least one percussion and vibration bladder. When the second rotary plate is in a second position and the first rotary plate is in the first position, the blower may be operable to inflate the left turn bladder. When the second rotary plate is in a third position and the first rotary plate is in the first position, the blower may be operable to inflate the right turn bladder. When the second rotary plate is in a fourth position and the first rotary plate is in the first position, the blower may be operable to move air through the patient interface. When the second rotary plate is in the first position and the first rotary plate is in a second position, the blower may be operable to deflate the at least one percussion and vibration bladder. When the second rotary plate is in the second position and the first rotary plate is in the second position, the blower may be operable to deflate the left turn bladder. When the second rotary plate is in the third position and the first rotary plate is in the second position, the blower may be operable to deflate the right turn bladder.

In some embodiments, the first angular displacement may be less than 90°. In some embodiments, the first angular displacement may be about 22.5°.

In some embodiments, the valve member may be rotatably oscillated back and forth through a second angular displacement that is smaller than the first angular displacement in the first direction and a second direction opposite to the first direction when the valve member is in the first position and when the valve member is in the second position so that oscillations in the positive pressure and negative pressure, respectively, are provided to the patient's airway. In some embodiments, the second angular displacement may be about 10°. In some embodiments, a frequency of oscillation of the valve member may be adjustable between about 1 Hertz and about 20 Hertz. In some embodiments, a motor may be operable to rotate and oscillate the valve member. In some embodiments, the motor may be a stepper motor. In some embodiments, the valve member may have a rotatable plate and the valve may have a pair of stationary plates between which the rotatable plate is sandwiched.

In some embodiments, a sensor may sense a beginning of an inspiration of the patient and control circuitry coupled to the sensor and to the valve. A control circuitry may signal the valve to move to the first position in response to the sensor sensing the beginning of the inspiration of the patient. The control circuitry may signal the blower to operate to provide the positive pressure to the airway of the patient at a positive target pressure. In some embodiments, the control circuitry may be coupled to the blower and to the valve. A graphical user interface may be coupled to the control circuitry. One or more of the following may be coupled to the control circuitry: a port for connection to a wireless communication module, a universal serial bus port, and a port for connection to a pulse oximetry device. In some embodiments, the graphical user interface may be operable to display one or more of the following: peak flow information, pressure information, flow information, volume information, a pressure graph, a volume graph, a flow graph, a flow vs. volume graph, and a pressure vs. time graph.

In some embodiments, the respiratory therapy device may be coupled to the head section of the frame. In some embodiments, the respiratory therapy device may be coupled to the seat section of the frame. In some embodiments, the respiratory therapy device may be coupled to the foot section of the frame.

In another aspect of the disclosed embodiments, a patient support apparatus includes a frame having a head section, a seat section, and a foot section. A mattress is positioned on the frame and extends across the head section, seat section, and foot section. The mattress includes a left turn bladder, a right turn bladder, and at least one percussion and vibration bladder. A respiratory therapy device is coupled to the frame. The respiratory therapy device includes a blower having an inlet and an outlet, a patient interface, and a valve including a valve member that is rotatable through a first angular displacement in a first direction from a first position to a second position. The outlet of the blower is coupled to the patient interface so that positive pressure is provided to a patient's airway via the patient interface when the valve member is in the first position. The inlet of the blower is coupled to the patient interface so that negative pressure is provided to the patient's airway via the patient interface when the valve member is in the second position. A rotary valve is coupled between a port of the respiratory therapy device and the patient interface. The rotary valve is coupled to the patient interface, the left turn bladder, the right turn bladder, and the at least one percussion and vibration bladder. The rotary valve includes a first rotary plate and a second rotary plate. When the second rotary plate is in a first position and the first rotary plate is in a first position, the blower is operable to inflate the at least one percussion and vibration bladder. When the second rotary plate is in a second position and the first rotary plate is in the first position, the blower is operable to inflate the left turn bladder. When the second rotary plate is in a third position and the first rotary plate is in the first position, the blower is operable to inflate the right turn bladder. When the second rotary plate is in a fourth position and the first rotary plate is in the first position, the blower is operable to move air through the patient interface.

In yet another aspect of the disclosed embodiments, a method of supplying airflow to a patient interface coupled to a patient support apparatus includes coupling a respiratory therapy device that is coupled to a frame of the patient support apparatus to the patient interface. The method also includes positioning a valve member of the respiratory therapy device in a first position to couple an outlet of a blower of the respiratory therapy device to the patient interface to provide positive pressure to a patient's airway via the patient interface. The method also includes positioning the valve member of the respiratory therapy device in a second position to couple an inlet of the blower of the respiratory therapy device to the patient interface to provide negative pressure to a patient's airway via the patient interface In some embodiments, the method requires coupling a housing to the frame. The method may also require positioning the respiratory therapy device within the housing. In some embodiments, the method requires positioning the respiratory therapy device in a drawer that slides in and out of the housing. In some embodiments, the method requires sliding the drawer into a closed position within the housing so that a port formed in the drawer and coupled to a port of the respiratory therapy device engages a port formed in the housing. In some embodiments, the method requires coupling the patient interface to the port formed in the housing with a hose. In some embodiments, the method requires coupling a port of the respiratory therapy device to a port formed in the frame. In some embodiments, the method requires coupling the port formed in the frame to the patient interface with a hose.

In some embodiments, a rotary valve may be coupled between a port of the respiratory therapy device and the patient interface, the rotary valve may be coupled to the patient interface, a left turn bladder of the mattress, a right turn bladder of the mattress, and at least one percussion and vibration bladder of the mattress. The rotary valve may have a first rotary plate and a second rotary plate. In some embodiments, the method requires positioning the second rotary plate in a first position when the first rotary plate is in a first position, and operating the blower to inflate the at least one percussion and vibration bladder. In some embodiments, the method requires positioning the second rotary plate in a second position when the first rotary plate is in the first position, and operating the blower to inflate the left turn bladder. In some embodiments, the method requires positioning the second rotary plate in a third position when the first rotary plate is in the first position, and operating the blower to inflate the right turn bladder. In some embodiments, the method requires positioning the second rotary plate in a fourth position when the first rotary plate is in the first position, and operating the blower to move air through the patient interface. In some embodiments, the method requires positioning the second rotary plate in the first position when the first rotary plate is in a second position, and operating the blower to deflate the at least one percussion and vibration bladder. In some embodiments, the method requires positioning the second rotary plate in the second position when the first rotary plate is in the second position, and operating the blower to deflate the left turn bladder. In some embodiments, the method requires positioning the second rotary plate in the third position when first rotary plate is in the second position, and operating the blower to deflate the right turn bladder.

In some embodiments, the first angular displacement may be less than 90°. In some embodiments, the first angular displacement may be about 22.5°.

In some embodiments, the method requires rotatably oscillating the valve member back and forth through a second angular displacement that is smaller than the first angular displacement in the first direction and a second direction opposite to the first direction when the valve member is in the first position and when the valve member is in the second position so that oscillations in the positive pressure and negative pressure, respectively, are provided to the patient's airway. In some embodiments, the second angular displacement may be about 10°. In some embodiments, a frequency of oscillation of the valve member may be adjustable between about 1 Hertz and about 20 Hertz.

In some embodiments, the method requires rotating and oscillating the valve member with a motor. In some embodiments, the method requires rotating and oscillating the valve member with a stepper motor.

In some embodiments, the method requires sensing with a sensor a beginning of an inspiration of the patient. In some embodiments, the method requires signaling with a control circuitry the valve to move to the first position in response to the sensor sensing the beginning of the inspiration of the patient. In some embodiments, the method requires signaling with the control circuitry the blower to operate to provide the positive pressure to the airway of the patient at a positive target pressure.

In some embodiments, the respiratory therapy device may be coupled to the head section of the frame. In some embodiments, the respiratory therapy device may be coupled to the seat section of the frame. In some embodiments, the respiratory therapy device may be coupled to the foot section of the frame.

According to another aspect of the disclosure, a patient support apparatus may include a bed that may include a frame, a mattress that may be supported by the frame, a respiratory therapy apparatus that may be supported by the frame, and a pneumatic system that may be operable to inflate at least one bladder of the mattress and operable to deliver air to the respiratory therapy apparatus.

The frame may include a siderail movable between a raised position and a lowered position and the respiratory therapy apparatus may include an output port coupled to the siderail. The frame may include a mattress support deck that may have a foot section and the pneumatic system may include an air source that may be coupled to the foot section. The pneumatic system may include a rotary valve that may be operable to deliver pulses to the mattress and to the respiratory therapy apparatus.

In some embodiments, the patient support apparatus may further include a graphical user interface that may be carried by the frame and operable to control the respiratory therapy apparatus. The frame may include a base frame and an upper frame that may be raiseable and lowerable relative to the base frame and the respiratory therapy apparatus may include at least one first component that may be coupled to the base frame and at least one second component that may be coupled to the upper frame. Optionally, the respiratory therapy apparatus may include at least one component that may be situated inside the mattress.

In some embodiments, the respiratory therapy apparatus may include a nebulizer. Alternatively or additionally, the respiratory therapy apparatus may include a filter. The respiratory therapy apparatus may include a blower and a compressor. The respiratory therapy apparatus may include a first patient interface coupleable to the blower and a second patient interface coupleable to the compressor. The first patient interface may include a filter and the second patient interface may include a nebulizer. The respiratory therapy apparatus may be controllable with a wireless device.

Additional features, which alone or in combination with any other feature(s), such as those listed above and/or those listed in the claims, can comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

Figure 1:
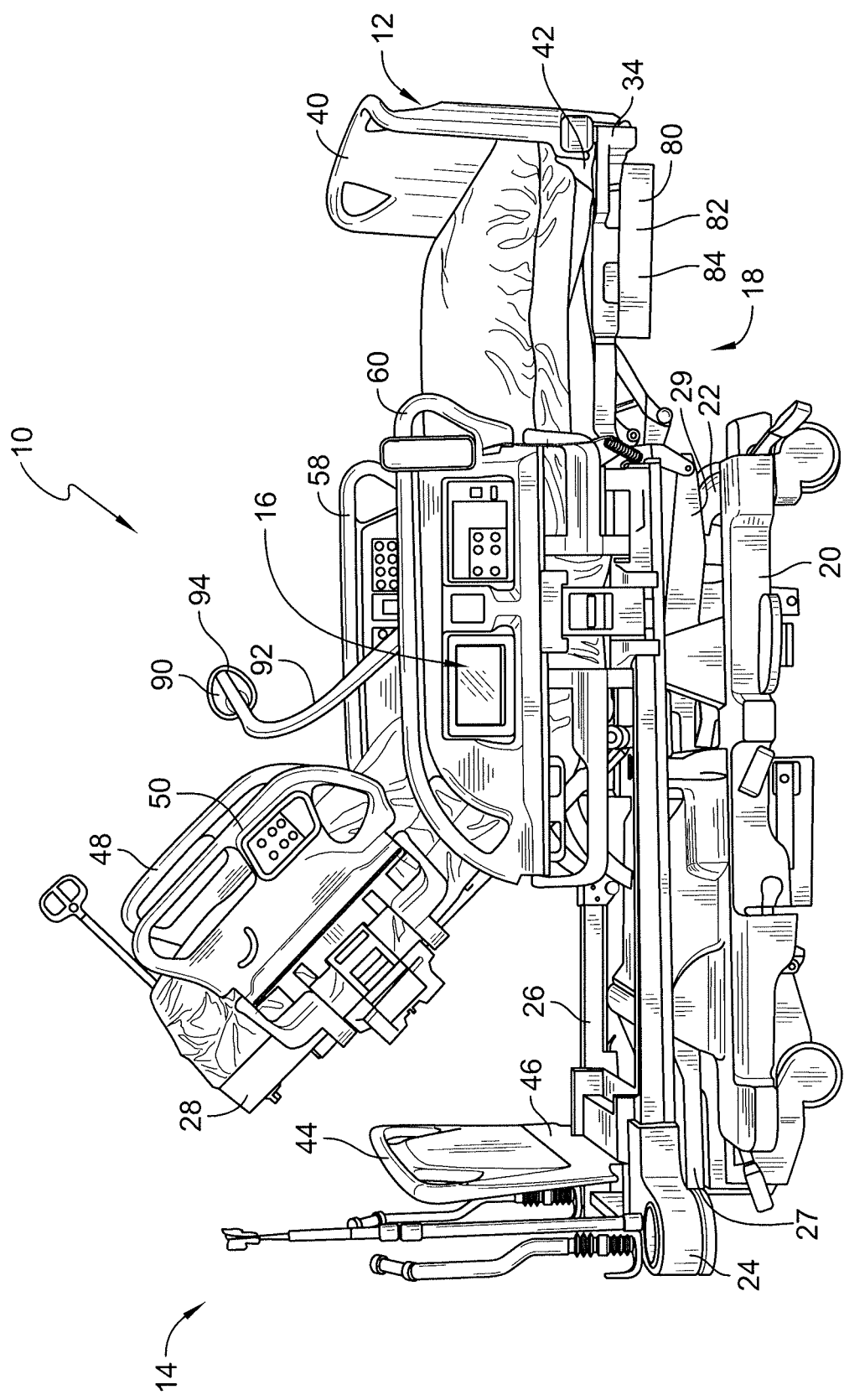
FIG. 1 is a side view of a patient support apparatus in accordance with an embodiment and having a housing attached thereto to house a respiratory therapy device.

Referring to FIG. 1, a patient support apparatus 10 is illustratively embodied as a hospital bed 10. The view shown in FIG. 1 is generally taken from a position that is oriented at the left side, foot end of the hospital bed 10. For purposes of orientation, the discussion of the hospital bed 10 will be based on the orientation of a patient supported on the hospital bed 10 in a supine position. Thus, the foot end 12 of the hospital bed 10 refers to the end nearest the patient's feet when the patient is supported on the hospital bed 10 in the supine position. The hospital bed 10 has a head end 14 opposite the foot end 12. A left side 16 refers to the patient's left when the patient is lying in the hospital bed 10 in a supine position. The right side 18 refers to the patient's right. When reference is made to the longitudinal length of the hospital bed 10, it refers a direction that is represented by the lines that generally extend between the head end 14 and foot end 12 of the hospital bed 10. Similarly, lateral width of the hospital bed 10 refers to a direction that is represented by the lines that generally extend between the left side 16 and right side 18.

The hospital bed 10 includes a base frame 20 which supports a lift system 22. The lift system 22 engages the base and an upper frame 24 such that the lift system 22 moves the upper frame 24 vertically relative to the base frame 20. The lift system 22 includes a head end linkage 27 and a foot end linkage 29. Each of the linkages 27 and 29 are independently operable and may be operated to cause the hospital bed 10 to move into a tilt position which is when the head end 14 of the upper frame 24 is positioned lower than the foot end 12 of the upper frame 24. The hospital bed 10 may also be moved to a reverse tilt position with the foot end 12 of the upper frame 24 is positioned lower than the head end 14 of the upper frame 24.

The upper frame 24 supports a load frame 26. The load frame 26 supports a head deck 28 which is movable relative to the load frame 26. The load frame 26 also supports an articulated seat deck, also movable relative to the load frame 26 and a fixed seat deck. Also supported from the load frame 26 is a foot deck 34 that is articulated and moveable relative to the load frame 26. The foot deck 34 in the illustrative embodiment of FIG. 1 provides for powered pivoting of the foot deck 34 and manual extension and retraction of the foot deck 34 to vary the length of the foot deck 34. In other embodiments, powered pivoting of the foot deck 34 may be omitted and the related movement may be caused manually, or follow movement of the articulated seat deck 30. In addition, in some embodiments, extension and retraction of the foot deck 34 may be powered by an actuator.

A foot panel 40 is supported from the foot deck 34 and extends vertically from an upper surface 42 to form a barrier at the foot end 12 of the hospital bed 10. A head panel 44 is positioned on an upright structure 46 of the base frame 20 and extends vertically to form a barrier at the head end 14 of the hospital bed 10. A left head siderail 48 is supported from the head deck 28 and is moveable between a raised position shown in FIG. 1 and a lowered position as is known in the art. A right head siderail 50 is also moveable between the raised position of FIG. 1 and lowered position.

The hospital bed 10 also includes a left foot siderail 58 and a right foot siderail 60, each of which is supported directly from the load frame 26. Each of the siderails 48, 50, 58, and 60 are operable to be lowered to a position below the upper surface 52. It should be noted that when the head deck 28 is moved, the head siderails 48 and 50 move with the head deck 28 so that they maintain their relative position to the patient. This is because both of the head siderails 48 and 50 are supported by the head deck 28.

A respiratory therapy device 100 (shown in FIG. 2) is coupled to the patient support apparatus 10. Respiratory therapy device 100 is positioned within a housing 82 coupled to foot end 12 of the patient support apparatus 10. In some embodiments, the respiratory therapy device 100 may be coupled to the head end 14 of the patient support apparatus 10 or at any location between the foot end 12 and the head end 14. The housing 82 includes a front wall 84 on which a display or graphical user interface (not shown) may be accessible to enter user inputs into device 100 and to view displayed information regarding the operation of device 100.

Device 100 is operable as an insufflation/exsufflation device or, as such devices are sometimes called, a cough assist device. Thus, device 100 is capable of applying positive pressure and negative pressure to a patient's airway, the positive pressure being applied during insufflation and the negative pressure being applied during exsufflation. The device 100 may be controlled to apply the positive insufflation pressure or the negative exsufflation pressure to the patient through a patient interface 90 that is coupled to an end of a hose 92, wherein the opposite end of the hose 92 is coupled to the respiratory therapy device 90. The user may select to switch between insufflation, exsufflation, and pause pressures. In some embodiments, device 100 is operable to provide other modes of respiratory therapy such as continuous positive expiratory pressure (CPEP) and continuous high frequency oscillation (CHFO), just to name a couple. CPEP and CHFO are sometimes referred to herein, collectively, as Intrapulmonary Percussive Ventilation (IPV). In the illustrative example, the patient interface 90 includes a mask 94 which is configured to engage a patient's face and generally seal the area around the patient's nose and mouth. In other embodiments, patient interface 90 includes a mouthpiece rather than the illustrative mask 94 and the mouthpiece has an end portion that a patient places inside his or her mouth.

Figure 2:
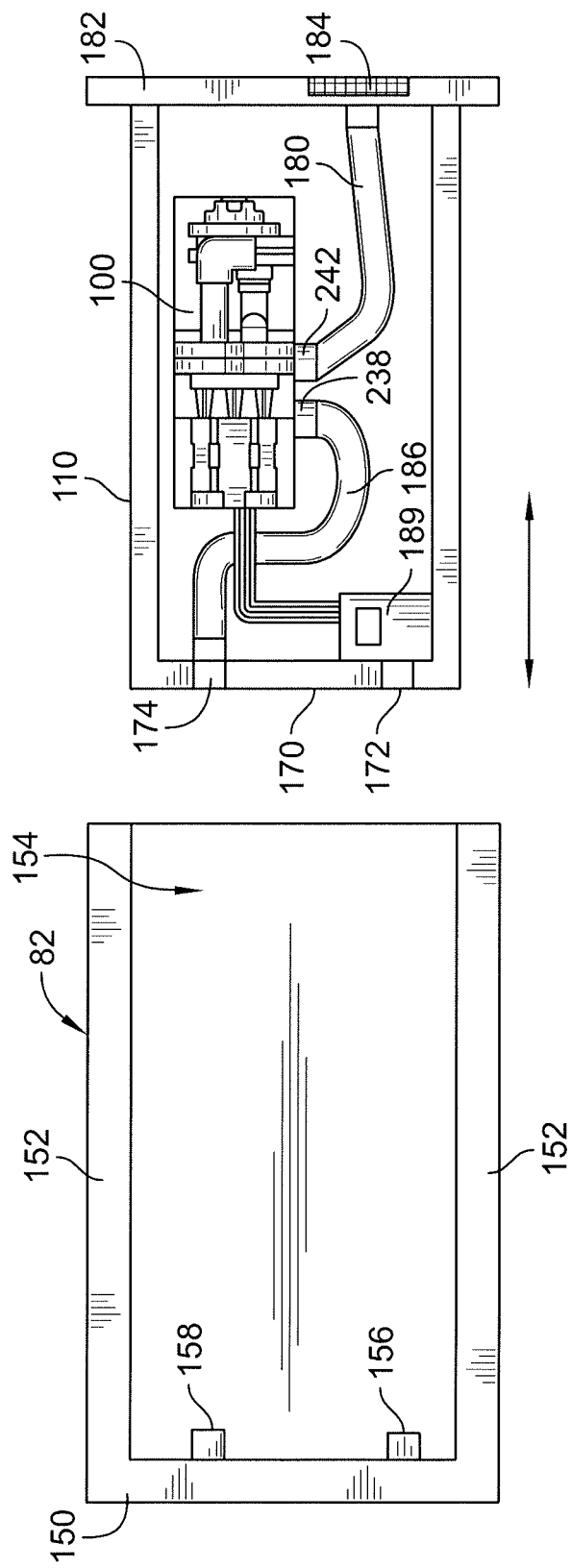
FIG. 2 is a plan view of the housing of FIG. 1 having the respiratory therapy device positioned therein.

Referring now to FIG. 2, the housing 82 includes a back wall 150, and a pair of sidewalls 152 that define an opening 154. An electrical port 156 and an air flow port 158 are positioned within the back wall 150. The electrical port 156 is coupled to a power source (not shown). The air flow port 158 coupled to the patient interface 90 via the hose 92. A drawer 110 is configured to slide into the opening 154 of the housing 82. The drawer 110 includes a back wall 170 having an electrical port 172 and an air flow port 174. When the drawer 110 is slid into the housing 82, the electrical port 172 electrically couples to the electrical port 156. Likewise, the air flow port 174 fluidly couples to the air flow port 158.

A respiratory therapy device 100 is positioned within the drawer 110. The respiratory therapy device 100 includes a port 238 and a port 242, which are described in more detail below. The port 242 is coupled to a hose 180 that extends through a front wall 182 of the drawer 110. A filter 184 may be positioned within the front wall 182 to filter air entering the respiratory therapy device 100. In some embodiments, the filter 184 is configured to be slid into an opening in the front wall 182 to facilitate changing the filter 184. The port 238 is coupled to the air flow port 174 via a hose 186 to enable air flow between the respiratory therapy device 100 and the patient interface 90, when the drawer 110 is slid into the housing 82. A power source 189, e.g. a battery, is positioned within the drawer 110 and is electrically coupled to the respiratory therapy device 100. The power source 189 powers the respiratory therapy device 100, when the drawer 110 is slid into the housing 82, such that the electrical port 172 electrically couples to the electrical port 156.

Figure 3:
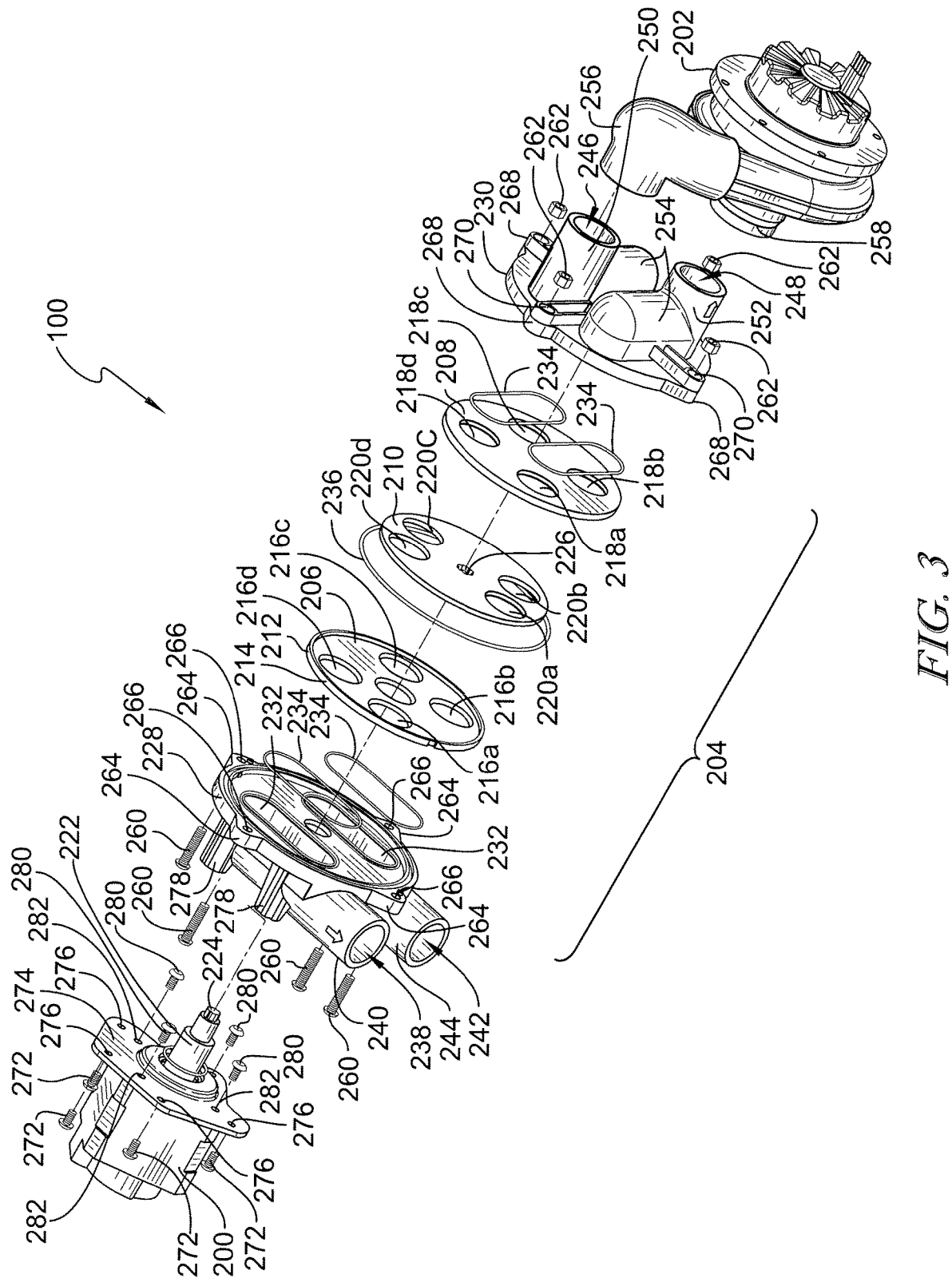
FIG. 3 is an exploded view of the respiratory therapy device of FIG. 2.

Referring now to FIG. 3, some components of a respiratory therapy device 100 are shown. The respiratory therapy device 100 is shown and described in Patent Cooperation Treaty Patent Application WO 2016/159889, filed Apr. 1, 2016, which is herein incorporated by reference in its entirety. Device 100 includes a stepper motor 200, a blower 202, and a rotary valve 204. Rotary valve 204 includes a first stationary plate 206, a second stationary plate 208, and a rotatable valve member or plate 210. Plates 206, 208, 210 are each circular or round in shape. Plate 210 is sandwiched between plates 206, 208. First stationary plate 206 has an annular rim 212 with an edge 214 that abuts plate 208. Rim 212 surrounds rotatable plate 210.

First stationary plate 206 has four holes 216a, 216b, 216c, 216d; second stationary plate 208 has four holes 218a, 218b, 218c, 218d; and rotatable plate 210 has four holes 220a, 220b, 220c, 220d. Holes 216a-d, 218a-d are aligned with each other. That is the "a-series" holes of plates 206, 208 are aligned; the "b-series" holes of plates 206, 208 are aligned; the "c-series" holes of plates 206, 208 are aligned; and the "d-series" holes of plates 206, 208 are aligned. An output shaft extension 222 of stepper motor 200 has a non-round tip 224 which is received in a complementarily shaped non-round aperture 226 provided at the center of rotatable plate 210. Thus, plate 210 rotates with output shaft extension 222 of stepper motor 200.

Stepper motor 200 acts through shaft 222 to rotate plate 210 so that various ones of holes 220a-d of rotatable plate 210 are aligned or misaligned with various ones of holes 216a-d, 218a-d of stationary plates 206, 208 to produce positive pressure, negative pressure, and oscillatory pressure to the patient interface 90. Rotatable plate 210 has a first position in which positive pressure from blower 202 is delivered to the patient interface 90 and a second position in which negative pressure from blower 202 is delivered to the patient interface 90. Plate 210 can be oscillated back and forth by stepper motor 200 with respect to the first position and with respective to the second position to produce oscillations in the pressure, be it positive or negative, provided at the patient interface 90.

Respiratory therapy device 100 has a first molded or cast manifold portion or shell 228 and a second molded or cast manifold portion or shell 230. Manifold shells 228, 230 are monolithic pieces that contain all of the passages that couple to holes 216a-d of stationary plate 206, in the case of shell 228, and to holes 218a-d of plate 208, in the case of shell 230. Shells 228, 230 have oblong openings 232 that communicate with respective pairs of holes 216a-d, 218a-d. Gaskets 234 are provided around oblong openings 232 to seal against respective stationary plates 206, 208. A large O-ring type gasket 236 provides a seal between manifold shells 228, 230. Gasket 236 encompasses a periphery of rotatable plate 210.

In FIG. 3, a passage 238 of shell 228 which couples to the patient interface 90 can be seen. Passage 238 is defined by a tubular portion 240 of shell 228. Shell 228 also has a passage 242 defined by a tubular portion 244 that communicates with atmosphere. Passage 238 of tubular portion 240 of manifold shell 228 communicates with holes 216a, 216d of stationary plate 206 through an associated oblong opening 232 and passage 242 of tubular portion 244 of manifold shell 228 communicates with holes 216b, 216c of stationary plate 206 through an associated oblong opening 232. Also in FIG. 3, passages 246, 248 of shell 230 can be seen. Passages 246, 248 are defined by tubular portions 250, 252 of shell 230, respectively. Passage 246 of tubular portion 250 of manifold shell 230 communicates with holes 218c, 218d of stationary plate 208 through an associated oblong opening (not shown, but similar to passages 232 of shell 228) and passage 248 of tubular portion 252 of manifold shell 230 communicates with holes 218a, 218b of stationary plate 206 through an associated oblong opening (not shown, but similar to passages 232, of shell 228). Manifold shell 230 has a pair of tubular connecting portions 254 in this regard to communicate with the oblong openings. Tubular portion 250 and its associated passage 246 of shell 230 couples to a positive pressure outlet of blower 202 via a first conduit 256. Similarly, tubular portion 252 and its associated passage 248 of shell 230 couples to the negative pressure inlet of blower 202 via a second conduit 258.

Suitable fasteners such as bolts or screws 260 and nuts 262 are provided to couple manifold shells 228, 230 together. In this regard, shell 228 has ears 264 with apertures 266 and shell 230 has ears 268 with nut-receiving bosses 270. Bolts 260 extend through ears 264, 268 are threaded into nuts 262 which are received in bosses 270. When shells 228, 230 are fastened together, plates 206, 208, 210 are sandwiched therebetween. Fasteners such as screws or bolts 272 are also provided to couple stepper motor 200 to manifold shell 228. In this regard, a plate 274 of stepper motor 200 has apertures 276 and manifold shell 228 has screw-receiving bosses 278 for receipt of fasteners 272. Screws 280 extend through apertures 282 to couple plate 274 of stepper motor 200.

Figure 4:
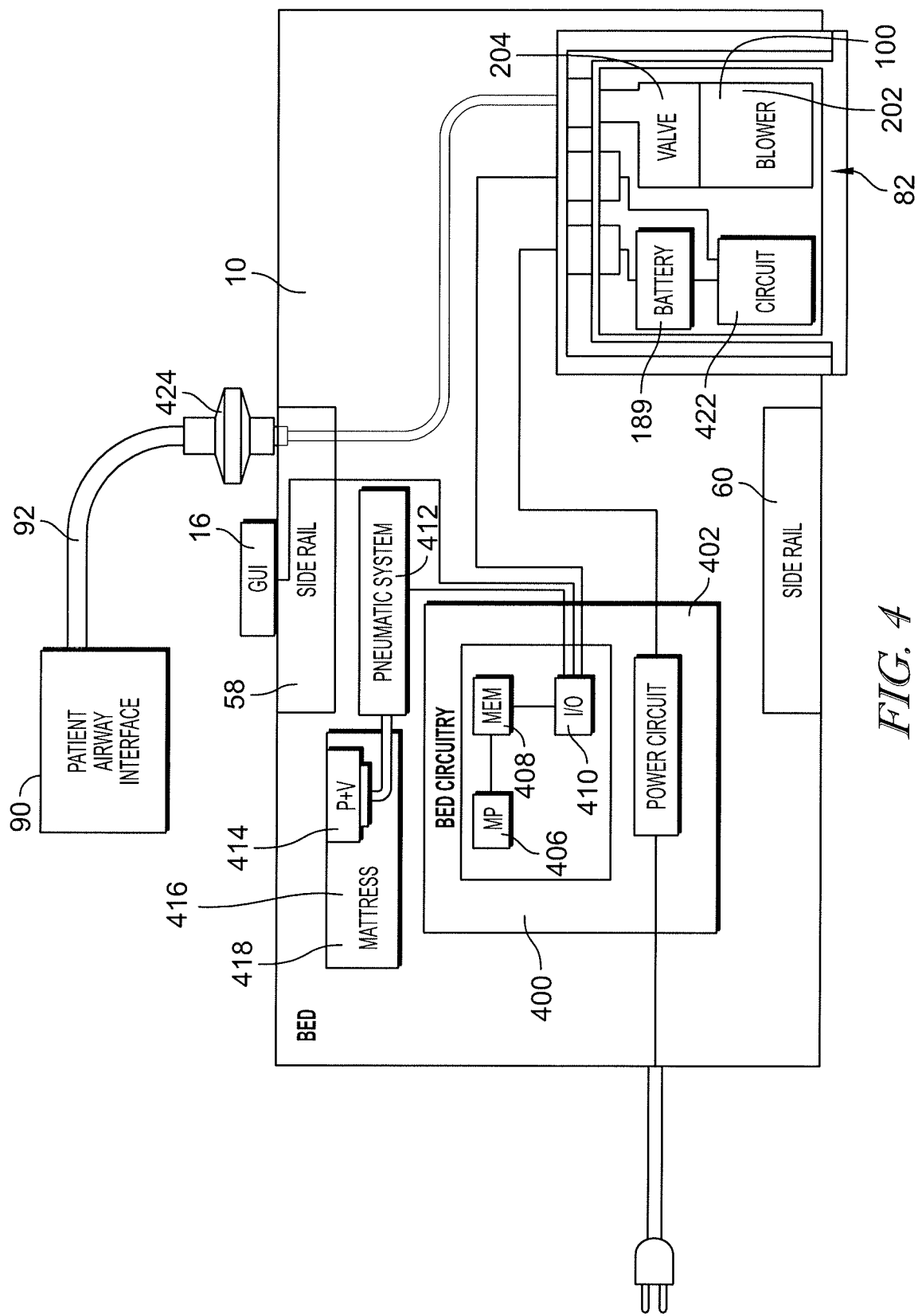
FIG. 4 is a schematic view of the patient support apparatus of FIG. 1 having the respiratory therapy device, a pneumatic system, and a control circuitry coupled thereto.

Referring to FIG. 4, the bed 10 includes a control unit 400 having control circuitry 402 that is powered by the power circuit 404. The control circuitry 402 includes micro-processor 406, memory 408, and an input/output (I/O) 410 connected to the GUI 16. The control circuitry 402 enables a user to operate various features of the bed 10 via the GUI 16.

A pneumatic system 412 is coupled to at least one percussion and vibration (P&V) bladder 414 and a plurality of mattress bladders, e.g. right turn bladder 416 and left turn bladder 418. The P&V bladder 414 is configured to send vibratory pulses to a zone of the bed 10. The right turn bladder 416 and left turn bladder 418 are configured to assist in turning a patient on the bed 10. In some embodiments, the bed 10 may include additional bladders coupled to the pneumatic system 412. The pneumatic system 412 receives inputs from the microprocessor 406 to control inflation and deflation of the bladders 416 and 418. In the case of the P&V bladders 414, the pneumatic system 412 receives inputs from the microprocessor 406 to control pulses sent to the P&V bladders 414. The pneumatic system 412 also sends outputs to the microprocessor 406 to monitor various data from the bladders 414, 416, 418, e.g. pressure. The data may be stored in the memory 408.

The respiratory therapy device 100 is positioned within the housing 82. The power source 189 and a control circuit 422 of the respiratory therapy device 100 are coupled to the I/O 410 so that the respiratory therapy device 100 may be controlled by a user at the GUI 16. The blower 202 and valve 204 are coupled to the circuit 422 to control airflow to the patient interface 90 via hose 92. In the illustrative embodiment, the patient interface 90 is shown with a removable filter 424. The patient interface 90 is also shown coupled to the left siderail 58. In some embodiments, the patient interface 90 may be coupled to the right siderail 60.

Figure 5:
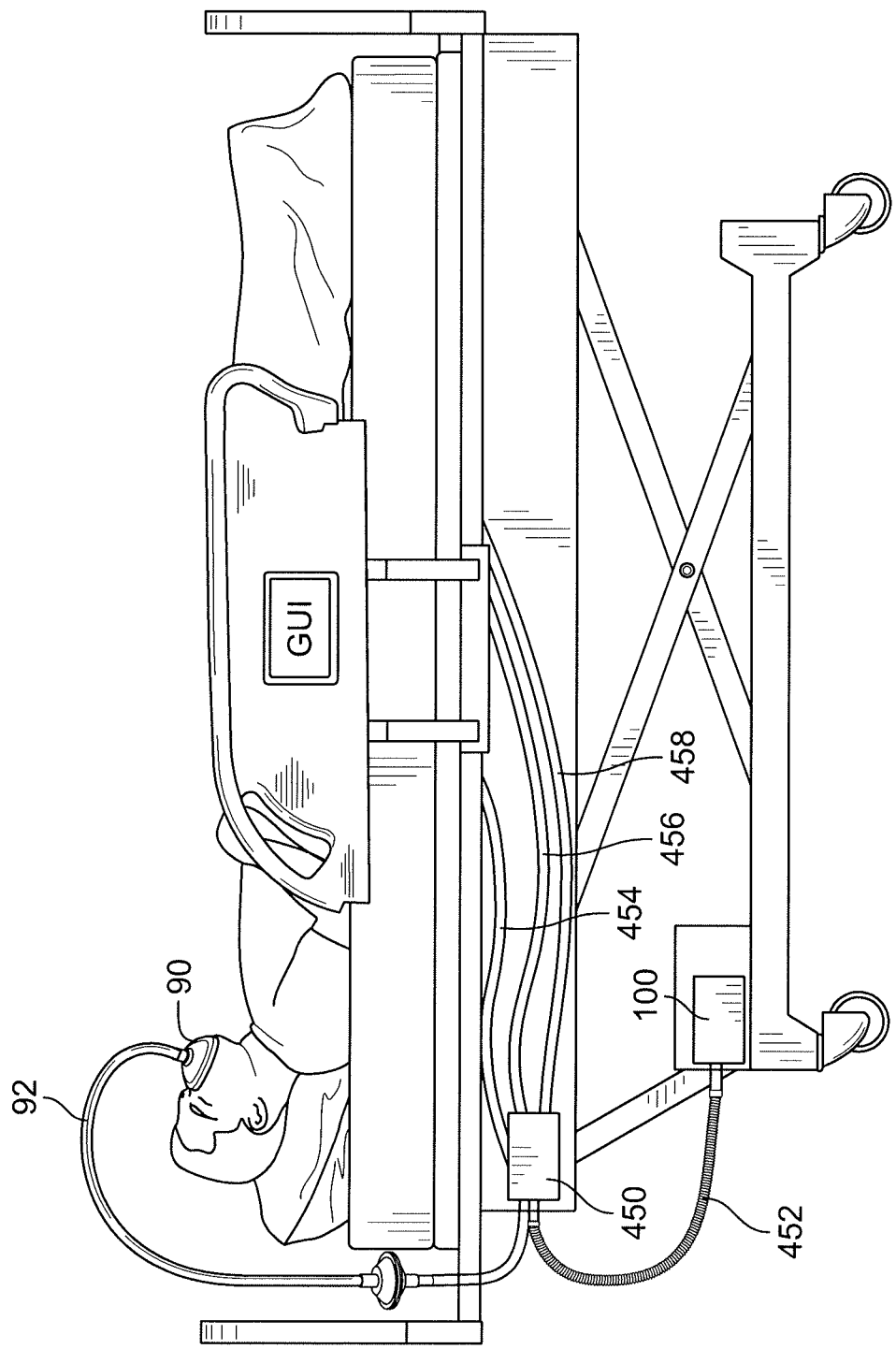
FIG. 5 is a side view of a patient support apparatus in accordance with an embodiment and having a respiratory therapy device and valve coupled thereto.

Referring to FIG. 5, the respiratory therapy device 100 may be coupled to a frame of the bed 10. A control valve 450 is coupled to the respiratory therapy device 100 via a hose 452. In the illustrative embodiment, the control valve 450 replaces pneumatic system 412. The hose 92 extends from the control valve 450 to the patient interface 90. Additionally, a hose 454 extends from the control valve 450 to P&V bladders 414. A hose 456 extends from the control valve 450 to right turn bladder 416. A hose 458 extends from the control valve 450 to left turn bladder 418. The control valve 450 receives air flow from the respiratory therapy device 100 and directs the air flow to one of P&V bladders 414, right turn bladder 416, and/or left turn bladder 418 as discussed in more detail below.

Figure 6:
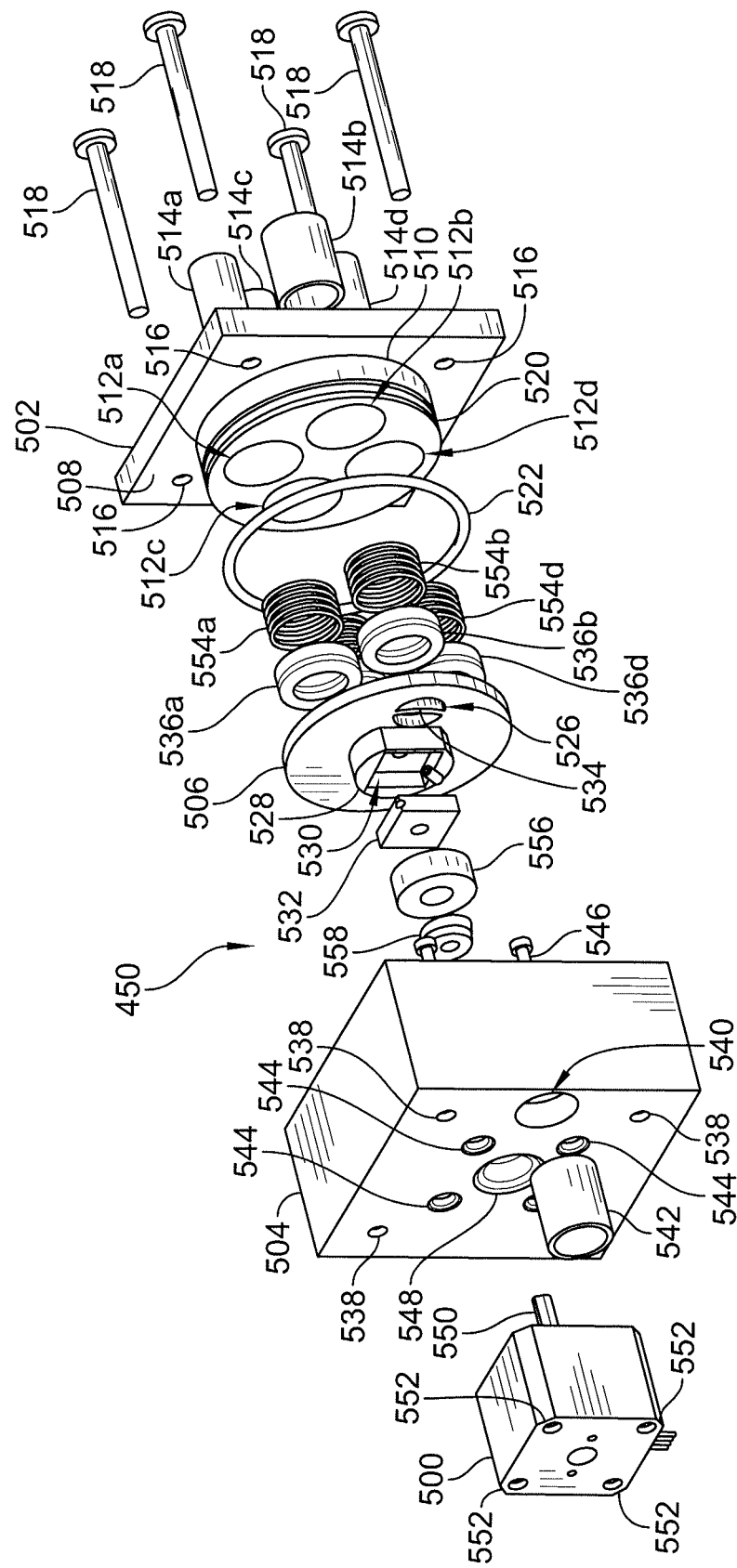
FIG. 6 is an exploded view of the valve of FIG. 5 taken from a first side.
Figure 7:
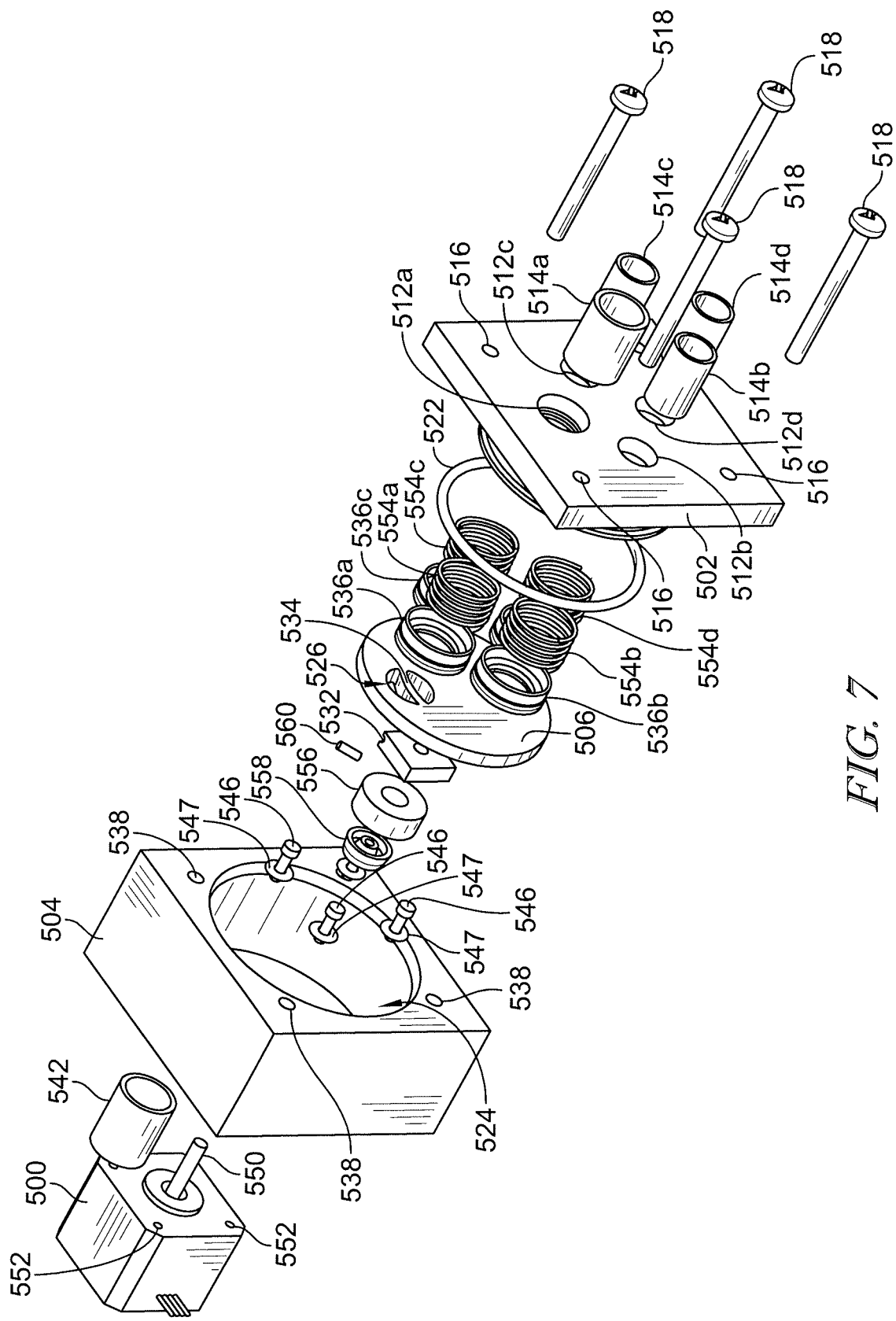
FIG. 7 is an exploded view of the valve of FIG. 5 taken from a second side.

Referring to FIGS. 6 and 7, the depicted components of the control valve 450 include a first stepper motor 500, cover 502, main block 504, and a rotatable plate 506. The control valve 450 is shown and described in U.S. Provisional Patent Application Ser. No. 62/483,636, filed Apr. 10, 2017, which is herein incorporated by reference in its entirety. There are further components sandwiched between the cover 502 and rotatable plate 506 and between the rotatable plate 506 and main block 504. The main block 504 and cover 502 are square in shape and the cover 502 has a flange 508 with a circular portion 510 projecting therefrom and having cylindrical holes 512a-512d to receive the tubes 514a-514d. The rotatable plate 506 is round in shape.

Flange 508 of cover 502 has four holes 516 to receive screws 518 to couple cover 502 to main block 504. The circular portion 510 of the cover 502 has a groove 520 that receives an O-ring 522. The O-ring 522 is made of a rubber or elastic material to provide sealing engagement between portion 510 of cover 502 and the inner surface of chamber 524. Thus, ring 522 provides a seal to prevent air from leaking from control valve 450 during operation. The tubular holes 512a-512d correspond to particular tubes 514a-514d so that air may be directed to the plurality of P&V bladders 414, turn assist bladder 416, turn assist bladder 418 or patient interface 90.

The rotatable plate 506 includes a hole 526 to allow for air flow through the rotatable plate 506 and a raised portion 528 that has a square hole 530 to receive a square block 532 to provide torque to the rotatable plate 506 from the first stepper motor 500. Rotary plate 506 includes a bar 534 across hole 526 to prevent cup seals 536a-536d sandwiched between the cover 502 and the rotatable plate 506 from herniating when the hole 526 is moved across the cup seals 536a-536d. Bar 534 bifurcates or separates hole 526 into two hole portions with each hole portion being on one side of bar 534 or the other. Springs 554a-554d bias the respective cup seals 536a-536d into engagement with the rotatable plate 506. The bar 534 comprises a curved piece across the hole 526 in the illustrative embodiment. Alternatively or additionally, the bar 534 may include straight portions. Bar 534, therefore, serves as an anti-herniation appendage situated in hole 526. In the illustrative embodiment, bar 534 extends all the way across 526.

The main block 504 includes four holes 538 that align with holes 516 of the cover 502 that receive the screws 518 to couple the cover 502 and the main block 504 together. The main block 504 includes an opening 540 to receive the passageway 542 therein. The main block 504 includes four holes 544 that receive suitable fasteners, such as bolts or screws 546 and washers 547, to couple the first stepper motor 500 to main block 504. The main block 504 also includes an opening 548 to receive an output shaft 550 of the first stepper motor 500. The first stepper motor 500 includes holes 552 to align with the holes 544 of the main block 504. Screws 546 are received in holes 544 of main block 504 and holes 552 of the first stepper motor 500.

The cover 502 and the rotatable plate 506 have springs 554a-554d compressed therebetween and in engagement with cup seals 536a-536d that align with the holes 512a-512d and the tubes 514a-514d. Thus, springs 554a-554d are compressed between cover 502 and the respective cup seal 536a-536d, each of which is, in turn, biased against rotary plate 506. The hole 526 of plate 506 rotates with the output shaft 550 to be positioned in alignment with one of the holes 512a-512d to allow airflow to the respective tube 514a-d which are, in turn, pneumatically coupled to respective P&V bladders 414, turn assist bladder 416, turn assist bladder 418 or patient interface 90.

A thrust bearing 556 is situated between the rotatable plate 506 and the main block 504 and helps to maintain the square portion 532 within the hole 530. A shaft seal 558 attaches to a distal end of the output shaft 550 and abuts the thrust bearing 556. The thrust bearing 556 abuts the square block 532. The first stepper motor 500 rotates the rotatable plate 506 through the output shaft 550 and the square block 532 received in the hole 530 of the rotatable plate 506. As shown in FIG. 7, main block 504 has cylindrical chamber 524 which receives the internal components of the control valve 450. A set screw 560 is provided to couple square block 532 to raised portion 528 of plate 506. Set screw 560 threads through raised portion 528 and into a hole formed at a corner region of the square block 532.

Figure 8:
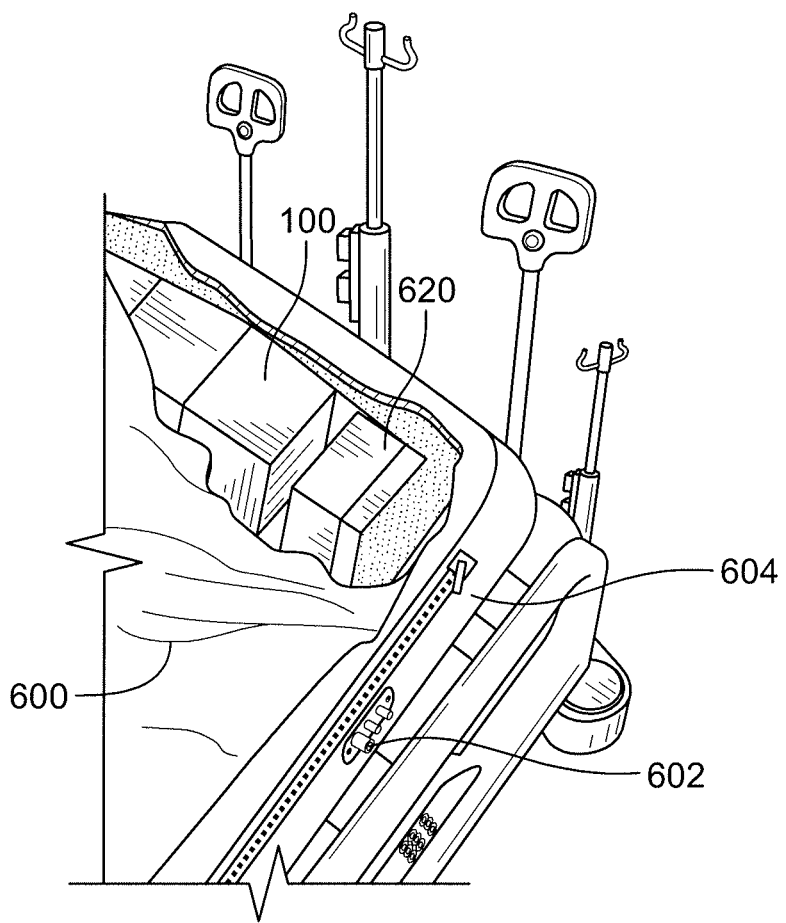
FIG. 8 is a perspective view of a patient support apparatus in accordance with an embodiment and having the respiratory therapy device and valve of FIG. 5 positioned within a support surface of the patient support apparatus.
Figure 9B:
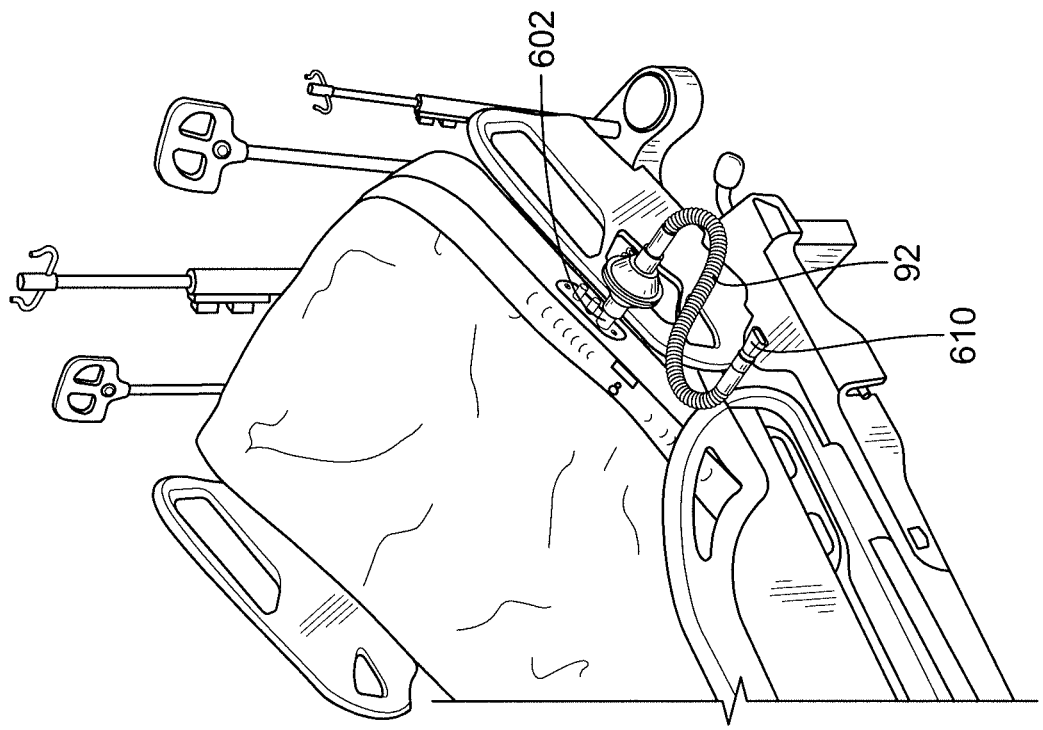
FIG. 9B is a perspective view of the patient support apparatus of FIG. 9A having a patient interface in the form of a mouthpiece coupled thereto.
Figure 9A:
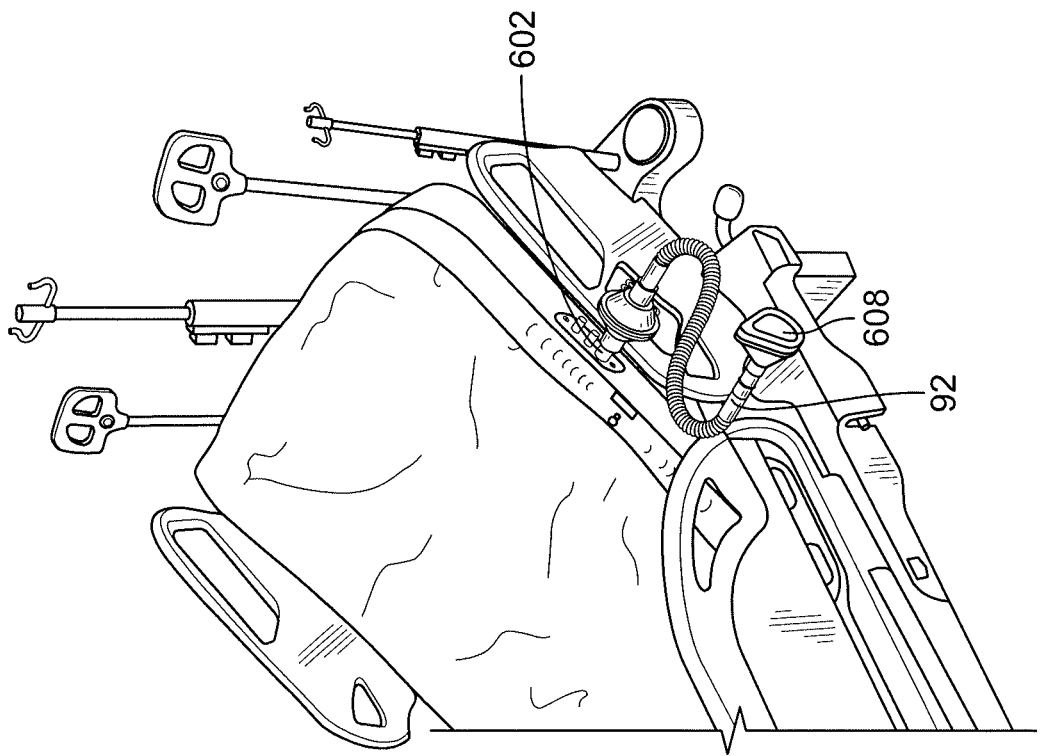
FIG. 9A is a perspective view of a patient support apparatus in accordance with an embodiment having a patient interface in the form of a mask coupled thereto.
Figure 10:
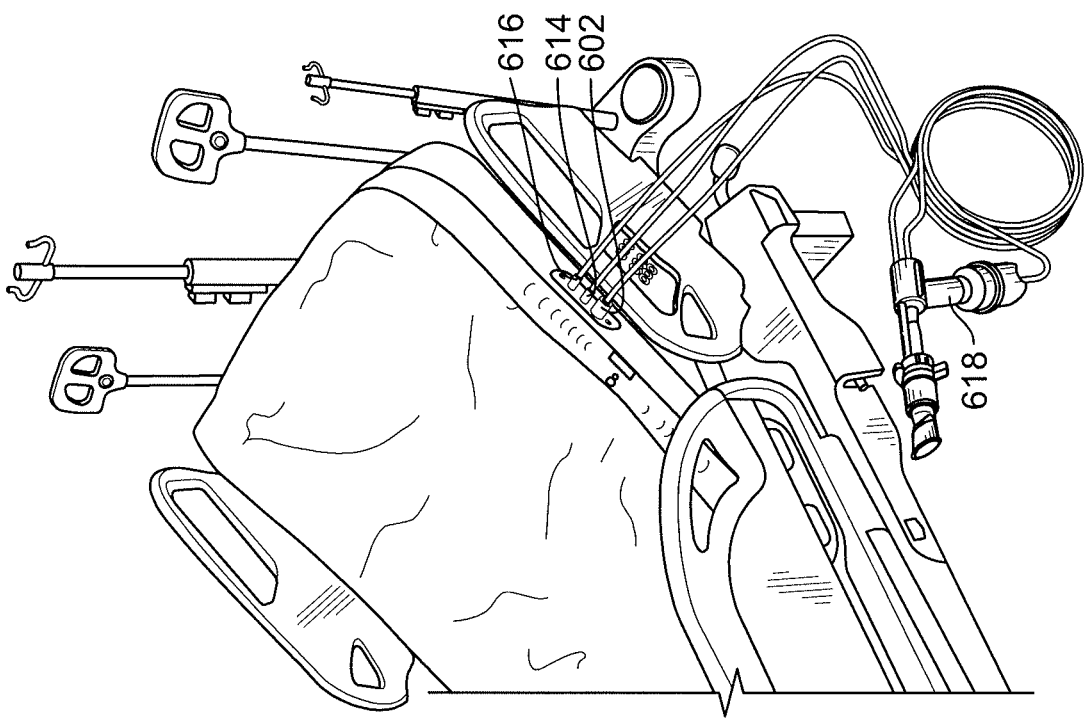
FIG. 10 is a perspective view of the patient support apparatus of FIG. 9A having a nebulizer coupled thereto.
Figure 9C:
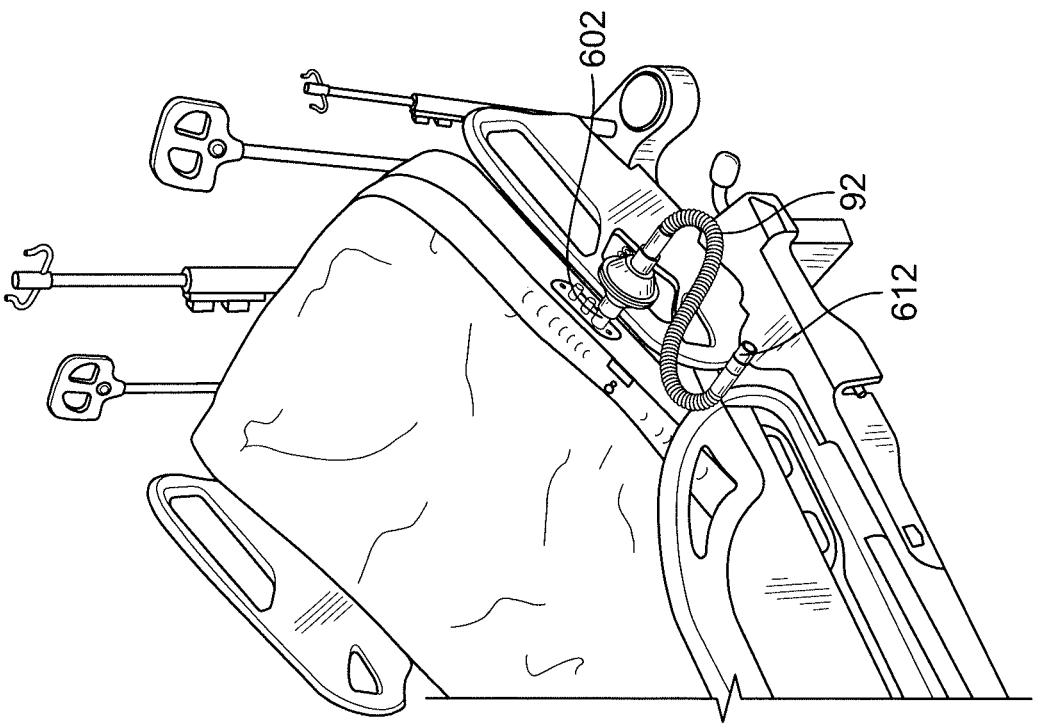
FIG. 9C is a perspective view of the patient support apparatus of FIG. 9A having a patient interface in the form of a tracheostomy tube coupled thereto.

Referring to FIG. 8, the respiratory therapy device 100 and a nebulizer pump 620 may be positioned within a mattress 600 of the bed 10. Outlets 602 may be positioned within a side 604 of the mattress 600 to control air flow to and from the respiratory therapy device. For example, a port 606 is provided to couple the hose 92 to the respiratory therapy device 100. Referring to FIGS. 9A-9C, different patient interfaces 90 may be connected to the hose 92. For example, a facemask 608 may be coupled to the hose 92, as shown in FIG. 9A. Alternatively or in addition to, a mouthpiece 610 may be coupled to the hose 92, as shown in FIG. 9B. Alternatively or in addition to, a tracheostomy tube 612 may be coupled to the hose 92, as shown in FIG. 9C. Referring to FIG. 10, additional ports 614 and 616 provide an inlet and outlet for coupling a nebulizer 618 to the nebulizer pump 620.

Figure 11:
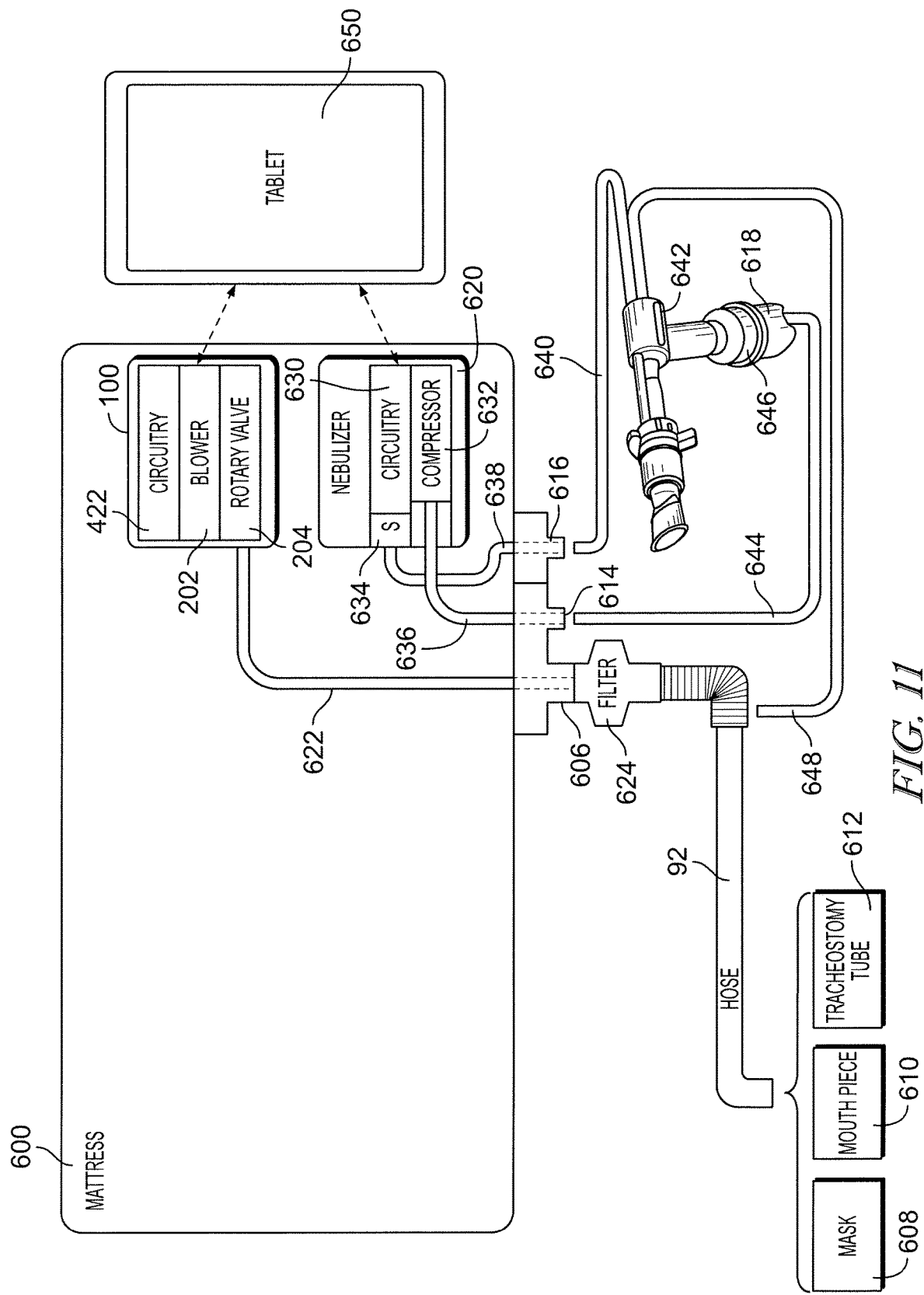
FIG. 11 is a schematic of the patient support apparatus of FIG. 9A.

The schematic shown in FIG. 11 illustrates the interchangeability of the facemask 608, mouthpiece 610, tracheostomy tube 612 and the nebulizer 618. The respiratory therapy device 100 and the nebulizer pump 620 are illustrated as being positioned within the mattress 600 of the bed 10. Alternatively, the respiratory therapy device 100 and the nebulizer pump 620 may be coupled to any part of the bed 10. The respiratory therapy device 100 includes the blower 202, valve 204, and control circuit 422 as described above. A tube 622 couples the respiratory therapy device 100 to the port 606. Through the port 606, the facemask 608, mouthpiece 610, and tracheostomy tube 612 may be interchangeably coupled to the hose 92. In the illustrated embodiment, a replaceable filter 624 may be coupled between the hose 92 and the port 606.

The nebulizer pump 620 includes a control circuitry 630 to control a compressor 632. A switch 634 alternates air flow to and from the compressor 632 to provide positive and negative air pressure to the nebulizer 618. A tube 636 couples the compressor 632 to the port 614, and a tube 638 couples the switch 634 to the port 616. A tube 640 couples the port 616 to an inlet/outlet 642 of the nebulizer 618. A tube 644 couples the port 614 to a mixing chamber 646 of the nebulizer 618. Additionally, when the facemask 608, mouthpiece 610, or tracheostomy tube 612 are not coupled to the port 606, a tube 648 may be extended between the inlet/outlet 642 of the nebulizer 618 and the port 606 to facilitate positive and negative pressure through the nebulizer 618.

Accordingly, utilizing ports 606, 614, and 616, the facemask 608, mouthpiece 610, tracheostomy tube 612, or nebulizer 618 may be interchangeably coupled to the respiratory therapy device 100. In the illustrated embodiment, a tablet 650 or other hand held device is in communication with the nebulizer pump 620 and the respiratory therapy device 100 to control operation of the nebulizer pump 620 and the respiratory therapy device 100. Alternatively, or in addition to, the nebulizer pump 620 and/or the respiratory therapy device 100 may be operated with the GUI 16 or any other suitable means. It should be noted that any of the systems or components described herein may be operated with the tablet 650, the GUI 16, or any other suitable device.

Although this disclosure refers to specific embodiments, it will be understood by those skilled in the art that various changes in form and detail may be made without departing from the subject matter set forth in the accompanying claims.

The invention claimed is:

1. A patient support apparatus comprising:
a frame having a head section, a seat section, and a foot section,
a mattress positioned on the frame and extending across the head section, seat section, and foot section,
a respiratory therapy device coupled to the frame, the respiratory therapy device having:
a blower having an inlet and an outlet,
a patient interface,
a valve including a valve member that is rotatable through a first angular displacement in a first direction from a first position to a second position, wherein the outlet of the blower is coupled to the patient interface so that positive pressure is provided to a patient's airway via the patient interface when the valve member is in the first position, wherein the inlet of the blower is coupled to the patient interface so that negative pressure is provided to the patient's airway via the patient interface when the valve member is in the second position, and
a rotary valve coupled between a port of the respiratory therapy device and the patient interface, the rotary valve being coupled to the patient interface, a left turn bladder of the mattress, a right turn bladder of the mattress, and at least one percussion and vibration bladder of the mattress.

2. The patient support apparatus of claim 1, further comprising a housing coupled to the frame, the respiratory therapy device positioned within the housing.

3. The patient support apparatus of claim 2, further comprising a drawer that slides in and out of the housing, the respiratory therapy device positioned within the drawer.

4. The patient support apparatus of claim 3, wherein:
the housing includes a wall having a port extending therethrough, and
the drawer includes a wall having a port coupled to a port of the respiratory therapy device,
wherein the port formed in the drawer engages the port formed in the housing when the drawer is slide into the housing in a closed position.

5. The patient support apparatus of claim 4, further comprising a hose coupling the patient interface to the port formed in the housing.

6. The patient support apparatus of claim 1, further comprising a port formed in the frame, a port of the respiratory therapy device coupled to the port formed in the frame.

7. The patient support apparatus of claim 6, further comprising a hose coupling the port formed in the frame to the patient interface.

8. The patient support apparatus of claim 1, wherein the respiratory therapy device is coupled to the foot section of the frame.

9. The patient support apparatus of claim 1, wherein the rotary valve includes a first rotary plate and a second rotary plate, when the second rotary plate is in a first position and the first rotary plate is in a first position, the blower is operable to inflate the at least one percussion and vibration bladder; when the second rotary plate is in a second position and the first rotary plate is in the first position, the blower is operable to inflate the left turn bladder; when the second rotary plate is in a third position and the first rotary plate is in the first position, the blower is operable to inflate the right turn bladder; and when the second rotary plate is in a fourth position and the first rotary plate is in the first position, the blower is operable to move air through the patient interface.

10. The patient support apparatus of claim 9, wherein when the second rotary plate is in the first position and the first rotary plate is in a second position, the blower is operable to deflate the at least one percussion and vibration bladder; when the second rotary plate is in the second position and the first rotary plate is in the second position, the blower is operable to deflate the left turn bladder; and when the second rotary plate is in the third position and the first rotary plate is in the second position, the blower is operable to deflate the right turn bladder.

11. The patient support apparatus of claim 1, wherein the first angular displacement is less than 90°.

12. The patient support apparatus of claim 11, wherein the first angular displacement is about 22.5°.

13. The patient support apparatus of claim 1, wherein the valve member is rotatably oscillated back and forth through a second angular displacement that is smaller than the first angular displacement in the first direction and a second direction opposite to the first direction when the valve member is in the first position and when the valve member is in the second position so that oscillations in the positive pressure and negative pressure, respectively, are provided to the patient's airway.

14. The patient support apparatus of claim 13, wherein the second angular displacement is about 10°.

15. The patient support apparatus of claim 13, wherein a frequency of oscillation of the valve member is adjustable between about 1 Hertz and about 20 Hertz.

16. The patient support apparatus of claim 1, further comprising a motor that is operable to rotate and oscillate the valve member.

17. The patient support apparatus of claim 16, wherein the motor comprises a stepper motor.

18. The patient support apparatus of claim 1, wherein the valve member comprises a rotatable plate and the valve comprises a pair of stationary plates between which the rotatable plate is sandwiched.

19. The patient support apparatus of claim 1, further comprising a sensor to sense a beginning of an inspiration of the patient and control circuitry coupled to the sensor and to the valve, the control circuitry signaling the valve to move to the first position in response to the sensor sensing the beginning of the inspiration of the patient, and the control circuitry signaling the blower to operate to provide the positive pressure to the airway of the patient at a positive target pressure.

20. The patient support apparatus of claim 1, further comprising control circuitry coupled to the blower and to the valve, a graphical user interface coupled to the control circuitry, and one or more of the following coupled to the control circuitry: a port for connection to a wireless communication module, a universal serial bus port, and a port for connection to a pulse oximetry device.

21. The patient support apparatus of claim 1, further comprising control circuitry coupled to the blower and to the valve and a graphical user interface coupled to the control circuitry, the graphical user interface being operable to display one or more of the following: peak flow information, pressure information, flow information, volume information, a pressure graph, a volume graph, a flow graph, a flow vs. volume graph, and a pressure vs. time graph.

22. The patient support apparatus of claim 1, wherein the respiratory therapy device is coupled to the head section of the frame.

23. The patient support apparatus of claim 1, wherein the respiratory therapy device is coupled to the seat section of the frame.

24. A patient support apparatus comprising:
a frame having a head section, a seat section, and a foot section,
a mattress positioned on the frame and extending across the head section, seat section, and foot section,
a respiratory therapy device coupled to the frame, the respiratory therapy device having:
a blower having an inlet and an outlet,
a patient interface,
a valve including a valve member that is rotatable through a first angular displacement in a first direction from a first position to a second position, wherein the outlet of the blower is coupled to the patient interface so that positive pressure is provided to a patient's airway via the patient interface when the valve member is in the first position, wherein the inlet of the blower is coupled to the patient interface so that negative pressure is provided to the patient's airway via the patient interface when the valve member is in the second position, and
control circuitry coupled to the blower and to the valve and a graphical user interface coupled to the control circuitry, the graphical user interface being operable to display one or more of the following: peak flow information, pressure information, flow information, volume information, a pressure graph, a volume graph, a flow graph, a flow vs. volume graph, and a pressure vs. time graph.

25. A patient support apparatus comprising:
a frame having a head section, a seat section, and a foot section,
a mattress positioned on the frame and extending across the head section, seat section, and foot section,
a respiratory therapy device coupled to the frame, the respiratory therapy device having:
a blower having an inlet and an outlet,
a patient interface, and
a valve including a valve member that is rotatable through a first angular displacement in a first direction from a first position to a second position, wherein the outlet of the blower is coupled to the patient interface so that positive pressure is provided to a patient's airway via the patient interface when the valve member is in the first position, wherein the inlet of the blower is coupled to the patient interface so that negative pressure is provided to the patient's airway via the patient interface when the valve member is in the second position,
wherein the valve member is rotatably oscillated back and forth through a second angular displacement that is smaller than the first angular displacement in the first direction and a second direction opposite to the first direction when the valve member is in the first position and when the valve member is in the second position so that oscillations in the positive pressure and negative pressure, respectively, are provided to the patient's airway.

26. A patient support apparatus comprising:
a frame having a head section, a seat section, and a foot section,
a mattress positioned on the frame and extending across the head section, seat section, and foot section,
a respiratory therapy device coupled to the frame, the respiratory therapy device having:
a blower having an inlet and an outlet,
a patient interface,
a valve including a valve member that is rotatable through a first angular displacement in a first direction from a first position to a second position, wherein the outlet of the blower is coupled to the patient interface so that positive pressure is provided to a patient's airway via the patient interface when the valve member is in the first position, wherein the inlet of the blower is coupled to the patient interface so that negative pressure is provided to the patient's airway via the patient interface when the valve member is in the second position, and
a sensor to sense a beginning of an inspiration of the patient and control circuitry coupled to the sensor and to the valve, the control circuitry signaling the valve to move to the first position in response to the sensor sensing the beginning of the inspiration of the patient, and the control circuitry signaling the blower to operate to provide the positive pressure to the airway of the patient at a positive target pressure.

* * * * *